United States Patent
Gershowitz

(10) Patent No.: US 7,291,139 B2
(45) Date of Patent: Nov. 6, 2007

(54) RETROGRADE CANNULA HAVING AUTOMATICALLY INFLATABLE BALLOON

(75) Inventor: Arthur D. Gershowitz, Ann Arbor, MI (US)

(73) Assignee: Terumo Cardiovascular Systems, Ann Arbor, MI (US)

( * ) Notice: Subject to any disclaimer, the term of this patent is extended or adjusted under 35 U.S.C. 154(b) by 506 days.

(21) Appl. No.: 10/963,050

(22) Filed: Oct. 12, 2004

(65) Prior Publication Data

US 2005/0085792 A1   Apr. 21, 2005

Related U.S. Application Data

(62) Division of application No. 10/082,098, filed on Feb. 26, 2002, now abandoned.

(51) Int. Cl.
*A61M 31/00* (2006.01)

(52) U.S. Cl. ...................................................... 604/509

(58) Field of Classification Search ............. 604/96.01, 604/248, 249, 264, 523, 537, 247, 103.01–103.14, 604/99.01–99.04, 101.01–103, 500, 508, 604/509; 606/192, 194, 195
See application file for complete search history.

(56) References Cited

U.S. PATENT DOCUMENTS

| | | | |
|---|---|---|---|
| 281,043 A | 7/1883 | Finney | |
| 3,742,960 A | 7/1973 | Dye et al. | |
| 5,021,045 A | 6/1991 | Buckberg et al. | |
| 5,100,385 A | 3/1992 | Bromander | |
| 5,395,331 A | 3/1995 | O'Neill et al. | |
| 5,695,468 A | 12/1997 | Lafontaine et al. | |
| 5,807,328 A * | 9/1998 | Briscoe | 604/102.02 |
| 6,102,891 A | 8/2000 | Maria Van Erp | |
| 6,176,843 B1 | 1/2001 | DiCaprio et al. | |
| 6,458,096 B1 * | 10/2002 | Briscoe et al. | 604/96.01 |

* cited by examiner

*Primary Examiner*—Matthew DeSanto
(74) *Attorney, Agent, or Firm*—Mark L. Mollon; Gael Diane Tisack

(57) ABSTRACT

Cardioplegia is delivered to a heart vessel by conducting the cardioplegia through an infusion lumen of a cannula. The cardioplegia communicates with a balloon disposed on a distal end of the cannula to cause the cardioplegia to inflate the balloon into sealing contact with a wall of the coronary sinus. The flow of cardioplegia is halted while preventing drainage of cardioplegia from the balloon, to maintain the balloon in its inflated state until such time as the flow of cardioplegia is resumed. Drainage of cardioplegia from the balloon is prevented by causing a valve to be shifted to a closed position blocking communication between the infusion lumen and the balloon. The valve can be shifted manually, or automatically in response to the halting of the delivery of cardioplegia.

6 Claims, 2 Drawing Sheets

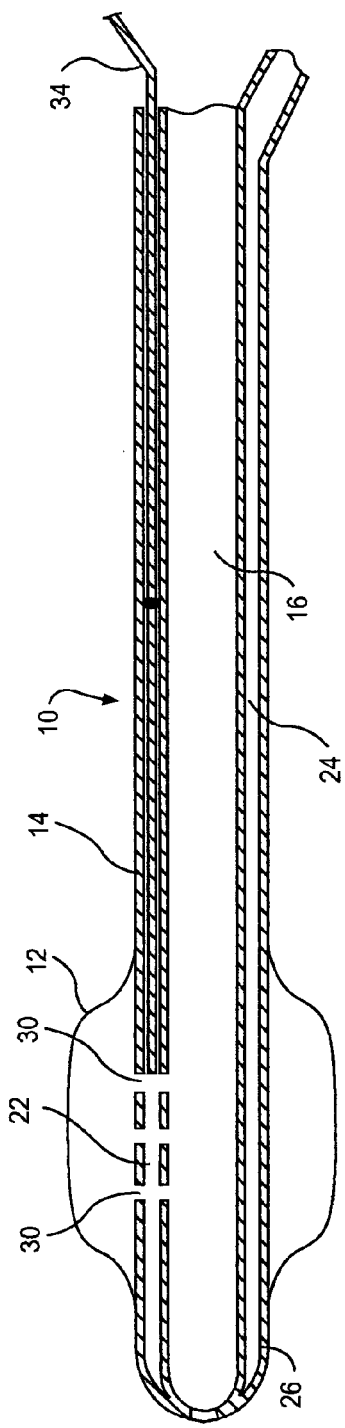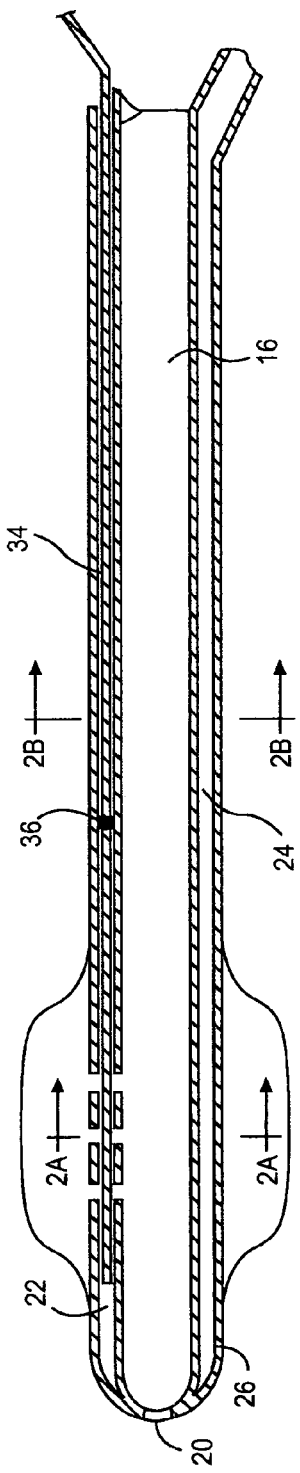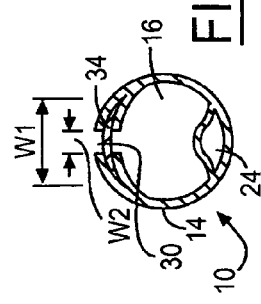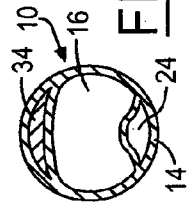

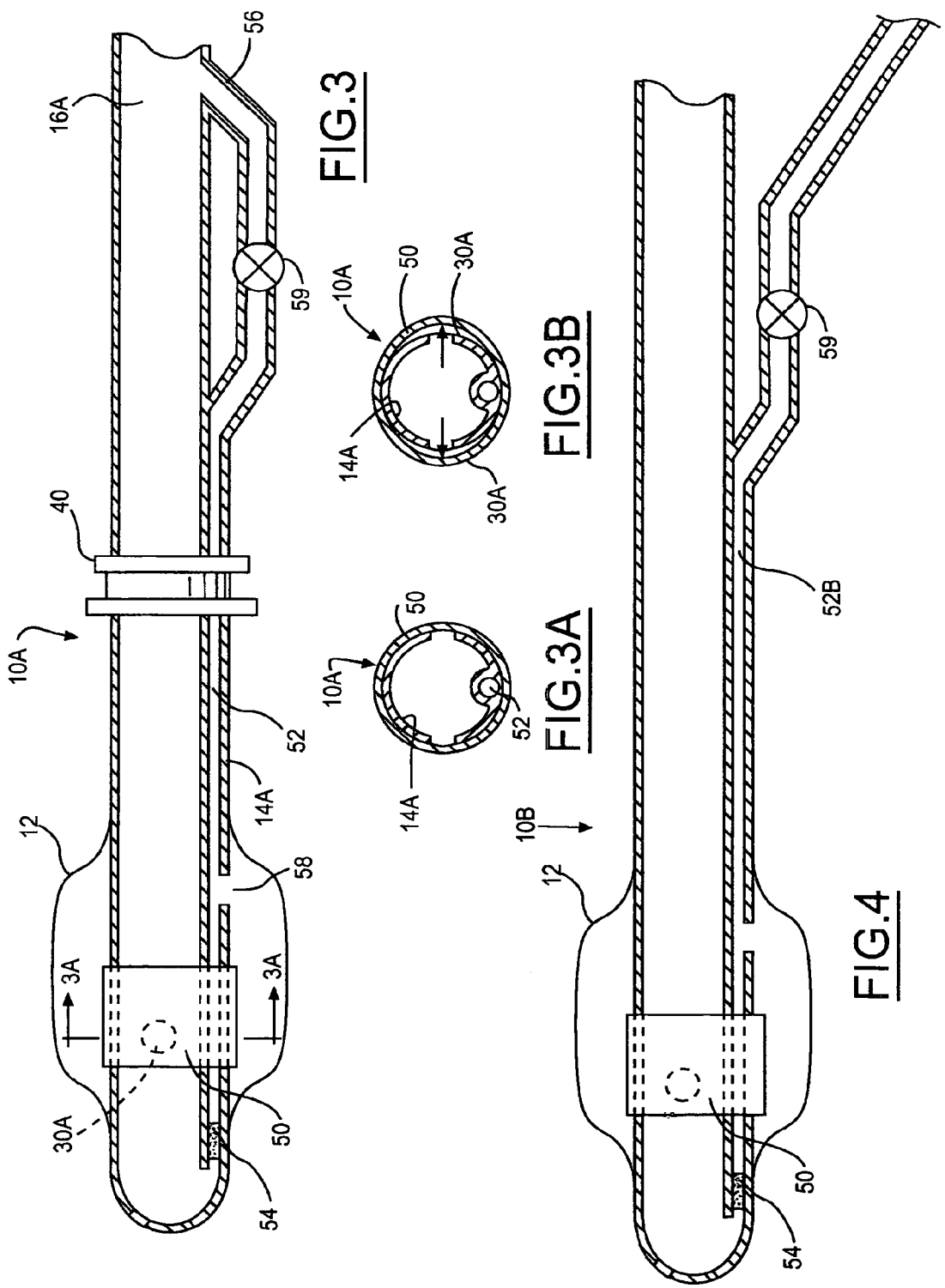

RETROGRADE CANNULA HAVING AUTOMATICALLY INFLATABLE BALLOON

This application is a division of application Ser. No. 10/082,098, filed Feb. 26, 2002 now abandoned.

BACKGROUND OF THE INVENTION

The present invention relates to balloon cannulas, and in particular to auto-inflate retrograde cannulas used in the delivery of cardioplegia.

Retrograde cannulas are commonly employed during certain cardiac surgical procedures, in order to deliver cardioplegia (CPG) into coronary veins to effect cardiac arrest of a patient by depolarizing cell membranes of the heart tissue (see U.S. Pat. No. 5,395,331).

In order to occlude the coronary sinus, the distal end of the cannula includes an inflatable balloon which, when inflated, seals against a wall of the coronary sinus. Balloons may be of the manual-inflating or auto-inflating type. In a manual-inflating type, a surgeon inflates the balloon by injecting a set amount (volume) of fluid therein. However, there exists a risk of over-inflation of the balloon, which can damage the coronary sinus.

The present invention pertains to the auto-inflating type (also referred to as self-inflating), wherein the balloon is in fluid communication with an infusion lumen of the cannula and is thus inflated by pressurized CPG being delivered to the heart. Thus, the risk of overinflation does not exist because the balloon is inflated to a pressure rather than to a volume as in the case of a manual-inflate balloon.

It will be apparent that the balloon of an auto-inflate cannula becomes deflated when the delivery of CPG is stopped. The cannula may thereafter be kept in place during the surgery in order to be able to periodically administer additional CPG. However, when the balloon becomes deflated, the distal end of the cannula may undergo unwanted displacement. This does not occur in the case of a manual-inflate cannula, but there occurs therein the risk of overinflation as described above.

Although it is common to affix the cannula in place by suturing the cannula to adjacent body tissue, the sutures are placed behind the balloon and thus are spaced by a few inches from the distal tip of the cannula. Thus, the portion of the cannula disposed ahead of the sutures may tend to shift. Such a tendency to shift is more prevalent during the delivery of warm CPG (and shiftable) than cold CPG, because the cannula is made more pliant by the warm CPG.

Since the ability of the distal end of the cannula to become displaced results from the deflation of the balloon, it would be desirable to enable the balloon of an auto-inflate retrograde balloon to stay inflated even when fluid is not being delivered through the cannula.

SUMMARY OF THE INVENTION

The present invention relates to a retrograde cannula for delivering fluid, such as cardioplegia, to a vessel, such as a vessel of the heart. The cannula comprises a body which includes proximal and distal ends and an infusion lumen extending therebetween for conducting pressurized fluid to a lumen outlet arrangement disposed adjacent the distal end. An automatically inflatable balloon extends around the body adjacent to, and spaced from, the lumen outlet arrangement. The balloon is receivable in the vessel in a deflated state and is inflatable into sealing contact with a wall of the vessel. The body includes a passage arrangement for fluidly communicating the balloon with the infusion lumen to enable the balloon to be inflated by the pressurized fluid conducted through the infusion lumen. A valve is arranged in the body for being shifted between an opened position to open the passage arrangement, and a closed position for closing the passage arrangement, to keep the balloon in its inflated state when the delivery of pressurized fluid is halted.

The valve can be manually shiftable between the opened and closed positions, or automatically shiftable between the opened and closed positions.

The invention also pertains to a method of delivering cardioplegia to a heart vessel. The method comprises the steps of:

A. positioning a distal end of a cannula within the heart vessel;

B. conducting a flow of pressurized cardioplegia through an infusion lumen of the cannula and discharging the cardioplegia into the heart vessel;

C. communicating the infusion lumen with a balloon disposed on the distal end to cause the cardioplegia to inflate the balloon into sealing contact with a wall of the heart vessel during step B;

D. halting the flow of cardioplegia through the infusion lumen while preventing drainage of cardioplegia from the balloon, to maintain the balloon in its inflated state; and E. thereafter repeating step B.

BRIEF DESCRIPTION OF THE DRAWINGS

The objects and advantages of the invention will become apparent from the following detailed description of preferred embodiments thereof in connection with the accompanying drawings in which like numerals designate like elements and in which:

FIG. 1 is a longitudinal sectional view through a cannula according to a first embodiment of the present invention, with a valve in an open position.

FIG. 2 is a view similar to FIG. 1 with the valve in a closed position.

FIG. 2A is a cross sectional view taken along the line 2A-2A in FIG. 2.

FIG. 2B is a cross sectional view taken along the line 2B-2B in FIG. 2.

FIG. 3 is a longitudinal sectional view taken through a cannula according to a second embodiment of the present invention.

FIG. 3A is a cross-sectional view taken along the line 3A-3A in FIG. 3, showing a valve in a closed position.

FIG. 3B is a view taken along the line 3A-3A in FIG. 3 with the valve in an open position.

FIG. 4 is a longitudinal sectional view through a third embodiment of the invention, with a valve in a closed position.

DETAILED DESCRIPTION OF PREFERRED EMBODIMENTS OF THE INVENTION

Depicted in FIGS. 1-2B is a retrograde cannula 10 having an automatically inflatable balloon adjacent its distal end. The cannula 10 includes a body 14 formed of a flexible plastic material suitable for insertion into a human body, such as PVC, urethane or silicone. Extending generally centrally through the body is an infusion lumen 16 capable of conducting a fluid, such as cardioplegia (CPG) from a proximal end of the cannula to one or more outlet openings 20 formed adjacent a distal end of the cannula. The outlet opening(s) may comprise forwardly-facing openings or side-facing openings.

Also formed in the cannula body 14 are a control lumen 22 and a pressure monitoring lumen 24 extending parallel to the infusion lumen. The pressure monitoring lumen 24 includes an opening 26 at its distal end for communicating with the interior of a vessel into which the cannula is to be inserted. The pressure monitoring lumen 24 serves as a pressure lumen to enable pressure in the vessel to be monitored.

Surrounding the body 14 adjacent the distal end thereof is the balloon 12. The balloon is secured to the body (or formed integrally with the body) in a conventional way and can be of conventional design. A passage arrangement formed by at least one, but preferably more than one, communication passages 30 places the balloon in fluid communication with the infusion lumen 16.

Preferably, the balloon is of the type that permanently assumes a predetermined shape and size whether inflated or not, and becomes stiff or turgid when inflated (in contrast to the type of balloon normally used in manual inflate cannulas that can contract into tight contact with the body when deflated).

The communication passages 30 are oriented to extend through the control lumen 22, as can be seen in FIG. 1. Moreover, a width W1 of the control lumen 22 is greater than a width W2 (e.g., diameter) of each communication passage. Disposed in the control lumen is a valve in the form of a slidable rod 34 having a width greater than that of each of the communication passages 30. Therefore, when the rod is slid forwardly toward the distal end of the body 14 (i.e., to the left in FIG. 1), so that the rod travels past the communication passages 30, the communication passages 30 will become closed. Thus, the rod is movable between an open position (FIG. 1) for opening the passages 30, and a closed position (FIG. 2) for closing the passages.

In order to ensure against leakage through the control lumen 22 when the rod 34 is in the open position (i.e., leakage to the right in FIG. 2), the rod 34 can be provided with a flexible seal element 36 which forms a seal against the wall of the control lumen.

In typical practice, the cannula 10 is inserted into a patient's body during cardiac surgery such that the distal end enters the coronary sinus. This is preferably performed with the aid of a stiff stylus (not shown) that has been temporarily inserted into the infusion lumen 16. Once the cannula has reached the desired position the stylus is removed and a suture ring (see the suture ring 40 shown in FIG. 3) of the cannula is sutured to the heart. With the rod 34 in its open position (FIG. 1, cardioplegia (CPG) is conducted under pressure through the infusion lumen 16, the CPG exiting the cannula through the discharge openings 20. Simultaneously, the CPG enters the balloon through the communication openings 30 and inflates the balloon into sealing relationship with the wall of the coronary sinus. Accordingly, the CPG is introduced into a cardiac sinus vessel, producing cardiac arrest. Then, the rod 34 is slid forwardly to the closed position (FIG. 2) to block the communication passages 30, and the flow of CPG through the infusion lumen is then temporarily halted.

Since the passages 30 are blocked, the balloon 12 remains firmly biased against the wall of the coronary sinus, to resist shifting of the distal end of the cannula. Accordingly, when the flow of CPG is resumed, the distal end of the cannula will still be disposed in the desired position.

Eventually, when the cannula is no longer needed, the balloon is deflated to enable it to be removed. That could be accomplished by moving the rod 34 to its open position to cause the cardioplegia in the balloon to flow back into the infusion lumen 16. Alternatively, a separate drain lumen could be provided for interconnecting the balloon and the infusion lumen, similar to the structure 52, 59 which will be described later in connection with FIGS. 3-3B.

It will be appreciated that the shape of the control lumen 22 and the rod 34 may vary as long as the rod is able to close the passages 30.

A second preferred embodiment of a cannula 10A is depicted in FIGS. 3-3B. In that embodiment, the control lumen and the rod are eliminated. Instead, the valve is in the form of an elastic membrane 50 which covers the communication passages 30A. The membrane 50 extends completely around the infusion lumen in the form of a band or sleeve formed of a suitable elastic plastic material. When CPG is conducted through the infusion lumen 16A, the pressurized CPG will force the sleeve 50 away from the passages 30 (i.e., to an open position) as shown in FIG. 3B, to enable the balloon 12A to be inflated. When the flow of CPG is halted, the sleeve will elastically rebound into tight contact with the wall of the lumen 16A to seal the passages 30 (as shown in FIG. 3A) and prevent the balloon from being deflated. Thus, the valve 50 opens and closes automatically, in contrast to the earlier disclosed valve 34 which is opened and closed manually.

When it is desired to remove the cannula 10A from the heart, the balloon is deflated by draining the CPG therefrom. That is achieved by a drain lumen 52 formed in the cannula body 14A. A distal end of the drain lumen 52 is closed off by a plug 54, and a proximal end 56 of the drain lumen communicates with the infusion lumen 16A. A drain hole 58 formed in the drain lumen communicates with the balloon interior, and a manually actuable valve 59 controls the drainage of the CPG from the balloon. The valve 59 can be of any suitable type, such as a stop-cock or tubing clamp for example. With the balloon in an inflated state, an opening of the drainage valve 59 will cause the balloon to deflate, with the draining CPG re-entering the infusion lumen 16A. Note also that the valve could be in the form of an external clamp, such as a hemostat or a tube or clamp, which blocks the escape of fluid from the balloon along the control lumen.

A third preferred embodiment of a cannula 10B is disclosed in connection with FIG. 4 and is similar to that of FIG. 3, except that the proximal end of the drain lumen 52B does not communicate with the infusion lumen. Note that in this cannula 10B, the removal of CPG from the drain lumen 52B, could be performed by forming the closure as a valve that can be opened. Alternatively, instead of allowing the CPG to drain freely through an opened valve, the CPG could be actively drained by being sucked through the drain lumen 52B using a suitable suction device, such as a syringe. In that event, the closure 59 could be in the form of a self-sealing plug through which the needle of the syringe could be inserted to withdraw fluid from the balloon. As a further alternative, the closure could comprise a syringe activated valve which would be used in conjunction with a syringe to withdraw fluid from the balloon. The withdrawal of CPG by a suction is particularly advantageous, because the suction can pull the balloon tightly against the body of the cannula, thereby reducing the profile of the cannula to facilitate passage thereof through the patient's body during insertion as well as removal of the cannula.

It will be appreciated that the present invention provides a way of preventing the auto-inflate balloon of a retrograde cannula from deflating between deliveries of CPL while the cannula remains in a patient's body, thereby keeping the distal end of the cannula in a desired state.

It will also be appreciated that numerous other types of manually or automatically operated valves could be employed in carrying out the invention, the ones disclosed herein merely being preferred.

Although the present invention has been described in connection with preferred embodiments thereof, it will be appreciated by those skilled in the art that additions, modifications, substitutions and deletions not specifically described may be made without departing from the spirit and scope of the invention as defined in the appended claims.

What is claimed is:

1. A method of delivering cardioplegia to a heart vessel, comprising the steps of:
   A. positioning a distal end of a cannula within the heart vessel;
   B. conducting a flow of pressurized cardioplegia through an infusion lumen of the cannula and discharging the cardioplegia into the heart vessel;
   C. communicating the infusion lumen through a passage arrangement with a balloon disposed on the distal end, during step B, to cause the cardioplegia to inflate the balloon into sealing contact with a wall of the heart vessel;
   D. halting the flow of cardioplegia through the infusion lumen while preventing drainage of cardioplegia from the balloon by causing a valve to move to a closed position closing the passage arrangement between the balloon and the infusion lumen to maintain the balloon in its inflated state with and without cardioplegia flowing in the infusion lumen; and
   E. then conducting a flow of pressurized cardioplegia through the infusion lumen of the cannula and discharging the cardioplegia into the heart vessel, while the valve is closed and the balloon is in its inflated state.

2. The method according to claim 1, further including, subsequent to step E, the step of draining cardioplegia from the balloon to reduce the profile thereof prior to withdrawal of the cannula from the heart vessel.

3. The method according to claim 2 wherein the draining step comprises sucking cardioplegia from the balloon by applying suction to the balloon interior.

4. The method according to claim 2 wherein the draining step comprises opening a drain lumen for draining cardioplegia from the balloon to the infusion lumen along a path different from the path along which the cardioplegia was conducted to the balloon in step C.

5. The method according to claim 1 wherein step D further comprises manually shifting the valve to the closed position.

6. The method according to claim 1, further comprising, subsequent to step E, the step of opening the vale to drain cardioplegia from the balloon to reduce the profile thereof prior to withdraw of the cannula from the heart vessel.

* * * * *